US008415334B2

(12) United States Patent
Burke et al.

(10) Patent No.: US 8,415,334 B2
(45) Date of Patent: Apr. 9, 2013

(54) METHOD OF COMBATING INFECTION

(75) Inventors: Philip John Burke, Salisbury (GB); Roger Melton, Salisbury (GB); Richard John Knox, Salisbury (GB)

(73) Assignee: Morvus Technology Ltd., Wiltshire (GB)

( * ) Notice: Subject to any disclaimer, the term of this patent is extended or adjusted under 35 U.S.C. 154(b) by 0 days.

(21) Appl. No.: 11/991,080

(22) PCT Filed: Sep. 4, 2006

(86) PCT No.: PCT/GB2006/003252
§ 371 (c)(1),
(2), (4) Date: Feb. 9, 2010

(87) PCT Pub. No.: WO2007/026166
PCT Pub. Date: Mar. 8, 2007

(65) Prior Publication Data
US 2010/0273762 A1 Oct. 28, 2010

(30) Foreign Application Priority Data
Sep. 3, 2005 (GB) .................................. 0517957.7

(51) Int. Cl.
*A61K 31/33* (2006.01)
(52) U.S. Cl.
USPC ........................................................ 514/183
(58) Field of Classification Search .................... 514/183
See application file for complete search history.

(56) References Cited

U.S. PATENT DOCUMENTS

| | | | |
|---|---|---|---|
| 3,208,999 | A | 9/1965 | Jarowenko et al. |
| 3,658,788 | A | 4/1972 | Orgel et al. |
| 4,251,536 | A | 2/1981 | Johnson |
| 4,375,394 | A | 3/1983 | Devon |
| 4,950,306 | A | 8/1990 | Marte et al. |
| 5,633,158 | A | 5/1997 | Anlezark et al. |
| 5,780,585 | A | 7/1998 | Anlezark et al. |
| 5,831,097 | A | 11/1998 | Ebel et al. |
| 5,873,912 | A | 2/1999 | Carlough |
| 5,977,065 | A | 11/1999 | Anlezark et al. |
| 2003/0228285 | A1 | 12/2003 | Hung et al. |
| 2004/0053208 | A1 | 3/2004 | Zavizion et al. |

FOREIGN PATENT DOCUMENTS

| | | |
|---|---|---|
| DE | 41 03 639 A1 | 8/1992 |
| EP | 0 330 432 A1 | 8/1989 |
| EP | 0 364 752 A2 | 4/1990 |
| EP | 0 540 263 | 5/1993 |
| EP | 0 540 263 A1 | 5/1993 |
| EP | 0 638 123 | 2/1995 |
| GB | 2 035 803 A | 6/1980 |
| GB | 2 365 338 A | 10/2001 |
| JP | 52 145 523 | 3/1977 |
| WO | WO 88/07378 A1 | 10/1988 |

(Continued)

OTHER PUBLICATIONS

International Search Report for PCT/GB2006/003252 mailed May 11, 2007.

(Continued)

*Primary Examiner* — Shengjun Wang
(74) *Attorney, Agent, or Firm* — Nixon & Vanderhye

(57) ABSTRACT

Method of combating a parasitic protozoal infection of a host organism, wherein the parasite causing the infection is associated with an enzyme system capable of activating tretazicar into a cytotoxic form. The method is carried out by administering tretazicar to the host organism.

13 Claims, 3 Drawing Sheets

FOREIGN PATENT DOCUMENTS

| WO | WO 93/08288 A1 | 4/1993 |
|---|---|---|
| WO | WO 95/35100 A1 | 12/1995 |
| WO | WO 96/03151 A2 | 2/1996 |
| WO | WO 97/23456 A1 | 7/1997 |
| WO | WO 98/35701 A1 | 8/1998 |
| WO | WO 98/52547 A1 | 11/1998 |
| WO | WO 98/57662 A2 | 12/1998 |
| WO | WO 99/32113 A1 | 7/1999 |
| WO | WO 99/61409 A1 | 12/1999 |
| WO | WO 00/10611 A2 | 3/2000 |
| WO | WO 01/64739 A1 | 9/2001 |
| WO | WO 02/30909 A1 | 4/2002 |
| WO | WO 2004/035769 A1 | 4/2004 |
| WO | WO 2005/002570 A1 | 1/2005 |
| WO | WO 2006/003492 A2 | 1/2006 |

OTHER PUBLICATIONS

Written Opinion for PCT/GB2006/003252 mailed May 11, 2007.

Workman, P., et al; "Pharmacology of the Mixed-Function Radio- and Chemosensitizers CB 1954 and RSU 1069"; *Int. J. Rad. Oncol. Biol. Phys.*; vol. 10(8); pp. 1307-1310 (1984).

Tisdale, M.J., et al; "Selective Inhibition of Ribonucleotide Reductase by the Monofunctional Alkylating Agent 5(1-Aziridinyl)-2,4-Dinitrobenzamide (DB 1954)"; *Biochem. Pharmacol.*; vol. 29(20); pp. 2845-2853 (1980).

Sunters, A., et al; "Cytotoxicitiy and Activation of CB1954 in a Human Tumour Cell Line"; *Biochem. Pharmacol.*; vol. 41(9); pp. 1293-1298 (1991).

Helsby, N.A., et al; "2-Amino metabolites are key mediators of CB 1954 and SN 23862 bystander effects in nitroreductase GDEPT"; *British Journal of Cancer*; vol. 90(5); pp. 1084-1092 (2004).

Tang, M. H.Y., et al; "Aerobic 2- and 4-nitroreduction of CB 1954 by human liver"; *Toxicology*; vol. 216(2-3); pp. 129-139 (2005).

Adams, G.E., et al; "Toxicity of Nitro Compounds Toward Hypoxic Mammalian Cell . . . Vitro: Dependence on Reduction Potential"; *J. Natl Cancer Inst.*; vol. 64, No. 3; pp. 555-5510 (1980).

Anlezark, G.M., et al; The Bioactivation of 5-(Aziridin-1-yl)-2,4-Dinitrobenzamide (CB1954)-I; Purification and Properties of a Nitroreductase Enzyme From *Escherichia coli*—A Potential Enzyme for Antibody-Directed Enzyme Prodrug Therapy (ADEPT); *Biochemical Pharmacoloty*; vol. 44, No. 12; pp. 2289-2295 (1992).

Connors, T.A., et al; "Studies on the Mechanism of Action of 5-aziridinyl-2,4-dinitrobenzamide (CB 1954), A Selective Inhibitor of the Walker Tumour"; *Int. J. Cancer*; vol. 7, pp. 86-92 (1971).

Friedlos, F., et al; "The Properties of Total Adducts and Interstrand Crosslinks in the DNA of Cells Treated with CB 1954; Exceptional Frequency and Stability of the Crosslink"; *Biochemical Pharmacology*; vol. 43, No. 6; pp. 1249-1254 (1992).

Knox, R.J., et al; "Quinone Reductase-Mediated Nitro-Reduction: Clinical Applications"; *Methods in Enzymology*; vol. 382; pp. 194 221 (2004).

Knox, R.J., et al; "Mechanism of Cytoxicity of Anticancer Platinum Drugs: Evidence That *cis*-Diamminedichloroplatinum(II) and *cis*-Diammine-(1,1-cyclobutanedicarboxylato)platinum(II) Differ Only in the Kinetics of Their Interaction with DNA"; *Cancer Research*; vol. 46; pp. 1972-1979 (1986).

Knox, R.J., et al; "The Bioactivation of 5-(Aziridin-1-yl)-2,4-Dinitrobenzamide (CB1954)-II; A Comparison of an *Escherichia coli* Nitroreductase and Walker DT Diaphorase"; *Biochemical Pharmacology*; vol. 44, No. 12, pp. 2297-2301 (1992).

Knox, R.J., et al; "Bioactivation of 5-(Aziridin-1-y1)-2,4-dinitrobenzamide (CB 1954) by Human NAD(P)H Quinone Oxidoreductase 2: A Novel Co-substrate-mediated Antitumor Prodrug Therapy"; *Cancer Research*; vol. 60, pp. 4179-4186 (2000).

Knox, R.J., et al; "The effect of monofunctional or difunctional platinum adducts and of various other associated DNA damage on the expression of transfected DNA in mammalian cell lines sensitive or resistant to difunctional agents"; *Biochemica et Biophysica Acta*; vol. 908; pp. 214-223 (1987).

Knox, R.J., et al; "The Walker 256 carcinoma: a cell type inherently sensitive only to those difunctional agents that can form DNA interstrand crosslinks"; *Mutation Research, DNA Repair*; vol. 255; pp. 227-240 (1991).

Li, Z., et al; "Nitrobenzocyclophosphamides as Potential Prodrugs for Bioreductive Activation: Synthesis, Stability, Enzymatic Reduction, and Antiproliferative Activity in Cell Culture"; *Bioorganic & Medicinal Chemistry*; vol. 11; pp. 4171-4178 (2003).

Malisza, K.L., et al; "Doxorubicin Reduces the Iron(III) Complexes of the Hydrolysis Products of the Antioxidant Cardioprotective Agent Dexrazoxane (ICRF-187) and Produces Hydroxyl Radicals"; *Archives of Biochemistry and Biophysics*, vol. 316, No. 2; pp. 680-688 (1995).

Skelly, J.V., et al; "Aerobic Nitroreduction by Flavoproteins: Enzyme Structure, Mechanisms and Role in Cancer Chemotherapy"; *Mini Reviews in Medicinal Chemistry*; vol. 1, No. 3; pp. 1-14 (2001).

Workman, P., et al; "CB 1954 revisited, II. Toxicity and antitumour activity"; *Cancer Chemotherapy and Pharmacology*; vol. 16; pp. 9-14 (1986).

Wu, K. et al; "Catalytic Properties of NAD(P)H: Quinone Oxidoreductase-2 (NQO2), a Dihydronicotinamide Riboside Dependent Oxidoreductase"; *Archives of Biochemistry and Biophysics*; vol. 347, No. 2; pp. 221-228 (1997).

Anlezark, G.M., et al; "Bioactivation of Dinitrobenzamide Mustards by an *E. coli* B Nitroreductase"; *Biochemical Pharmacology*; vol. 50, No. 5; pp. 609-618 (1995).

Apple, M.A., et al; Arrest of Cancer in Mice by Therapy with Normal Metabolites, II. Indefinite Survivors Among Mice Treated with Mixtures of 2-oxopropanal (NSC-79019) and 2,3-dihydroxypropanal (NSC-67934); *Cancer Chemotherapy Reports (Part 1)*; vol. 52, No. 7; pp. 687-696 (1968).

Bailey, S.M., et al; "Investigation of alternative prodrugs for use with *E. coli* nitroreductase in 'suicide gene' approaches to cancer therapy"; *Gene Therapy*; vol. 3; pp. 1143-1150 (1996).

Bridgewater, J.A., et al; "The Bystander Effect of the Nitroreductase/CB1954 Enzyme/Prodrug System Is Due to a Cell-Permeable Metabolite"; *Human Gene Therapy*; vol. 8; pp. 709-717 (1997).

CAPLUS Abstract No. 1966: 68533; Ilg, H., et al; "Possible applications of reductonates in the fixation of vat dyes by the two-stage printing process"; *Textil-Praxis*; vol. 20; No. 11; pp. 916-920 (1965).

CAPLUS Abstract No. 1967: 17926, Von Ardenne, M.; *Naturwissenschaften*; vol. 51, pp. 217-218 (1964).

Chen, S., et al; "Molecular Basis of the Catalytic Differences among DT-diaphorase of Human, Rat, and Mouse"; *The Journal of Biological Chemistry*; vol. 272, No. 3; pp. 1437-1439 (1997).

Chen, S., et al; "Catalytic Properties of NAD(P)H:Quinone Acceptor Oxidoreductase: Study Involving Mouse, Rat, Human, and Mouse-Rat Chimeric Enzymes"; *Molecular Pharmacology*; vol. 47; pp. 934-939 (1995).

Cobb, L.M.; "Toxicity of the Selective Antitumor Agent 5-Aziridino-2,4-Dinitrobenzamide in the Rat"; *Toxicology and Applied Pharmacology*; vol. 17; pp. 231-238 (1970).

Cui, W., et al; "Inducible Ablation of Astrocytes Shows That These Cells are Required for Neuronal Survival in the Adult Brain"; *GLIA*; vol. 34; pp. 272-282 (2001).

Cui, W., et al; "Nitroreductase-mediated cell ablation is very rapid and mediated by a p53-independent apoptotic pathway"; *Gene Therapy*; vol. 6; pp. 764-770 (1999).

Ernster, L., ". . . Diaphorase: A Historical Review"; *Scripta*; vol. 27A, pp. 1-13 (1987).

Felmer, R., et al; "Inducible ablation of adipocytes in adult transgenic mice expressing the *E. coli* nitroreductase gene"; *Journal of Endocrinology*; vol. 175; pp. 487-498 (2002).

Friedlos, F., et al; "Gene-directed enzyme prodrug therapy: quantitative bystander cytotoxicity and DNA damage induced by CB1954 in cells expressing bacterial nitroreductase"; *Gene Therapy*; vol. 5, pp. 105-112 (1998).

Gutierrez, P.L.; "The Metabolism of Quinone-Containing Alkylating Agents: Free Radical Production and Measurement"; *Frontiers in Bioscience*; vol. 5; pp. 629-638 (2000).

Hauge, J.G., et al; "Oxidation of Dihydroxyacetone Via the Pentose Cycle in Acetobacter Suboxydans"; *The Journal of biological Chemistry*; vol. 214; pp. 11-26 (1955).

Heller, J., et al; "Reduction by Non-sugar Compounds Occurring in Biological Material"; *Bulletin de l Academie Polonaise des Sciences*; vol. 16, No. 7; pp. 401-405 (1968).

Hu, L., et al; "Nitroaryl Phosphoramides as Novel Prodrugs for *E. coli* Nitroreductase Activation in Enzyme Prodrug Therapy"; *J. Med. Chem.*; vol. 46; pp. 4818-4821 (2003).

Isles, A.R., et al; "Conditional Ablation of Neurones in Transgenic Mice"; *J. Neurobiol.*; vol. 47; pp. 183-193 (2001).

Kammerer, C., et al; "Synergistic Effect of Dehydroascrobic Acid and Mixtures with Vitamin E and β-Carotene on Mitomycin C Efficiency Under Irradiation In Vitro"; *In Vivo*; vol. 18; pp. 795-798 (2004) XP-009082485.

Knox, R.J., et al; "Identification, Synthesis and Properties of 5-(Azindin-1-yl)-2-Nitro-4-Nitrosobenzamide, A Novel DNA Crosslinking Agent Derived From CB1954"; *Biochemical Pharmacology*; vol. 46, No. 5; pp. 797-803 (1993).

Ma, D., et al; "Selective ablation of olfactory receptor neurons without functional impairment of vomeronasal receptor neurons in OMP-ntr transgenic mice"; *European Journal of Neuronscience*; vol. 16; pp. 2317-2323 (2002).

Mauger, A.B., et al; Self-Immolative Prodrugs: Candidates for Antibody-Directed Enzyme Prodrug Therapy in Conjunction with a Nitroreductase Enzyme; *Journal of Medicinal Chemistry*; vol. 37, No. 21; pp. 3452-3458 (1994).

Nelson, N.; "A Photometric Adaptation of the Somogyi Method for the determination of Glucose"; *The Journal of Biological Chemistry*; vol. 153; pp. 375-380 (1944).

Neumuller, A.-O.; *Rompps Chemie-Lexikon*; 8th edition; p. 1513; inc. English language translation; (ISBN 3-440-04510-2) (1981) XP-002430266.

PhD Thesis by Jonathan D. Wright; Univ. of Essex; p. 13-28.

Post, J., et al; "The Replication Time and Pattern of the Liver Cell in the Growing Rat"; *J. Cell. Biol.*; vol. 18, pp. 1-12.

Prochaska, H.J., et al; "Purification and Characterization of Two Isofunctional Forms of NAD(P)H:Quinone Reductase from Mouse Liver"; *The Journal of Biological Chemistry*; vol. 261, No. 3; pp. 1372-1378 (1986).

Rauth, A.M., et al; "Bioreductive Therapies: An Overview of Drugs and Their Mechanisms of Action"; *Int. J. Rdiation Oncology Biol. Phys.*; vol. 42, No. 4; pp. 755-762 (1998) XP-002131257.

Ross, W.C.J.; "A spectrophotometric method for the estimation of the carcinostatic agent, 5-aziridino-2,4-dinitrobenzamide (CB 1954), in biological fluids"; *Biochemical Pharmacology*; vol. 18; pp. 2683-2688 (1969).

Sheard, C.E., et al; "The Sensitivity to Chemotherapeutic Agents of a Rat Tumour Grown in Immuosuppressed Mice"; *Br. J Cancer*; vol. 25; pp. 838-844 (1971).

Wolkenberg, S.E., et al; "In situ activation of antitumor agents"; *Tetrahedron Letters*; pp. 1-5 (2001).

Workman, P., et al; "CB 1954 Revisited, I. Deposition kinetics and metabolism"; *Cancer Chemother Pharmacol.*; vol. 16; pp. 1-8 (1986).

Wu, K., et al; "Demonstration of the Activation of Prodrug CB 1954 Using Human DT-Diaphorase Mutant Q104Y-Transfected MDA-MB-231 Cells and Mouse Xenograft Model"; *Archives of Biochemistry and Biophysics*; vol. 385, No. 1; pp. 203-208 (2001).

Angyal, S.J., et al; "The Composition of Reducing Sugars in Aqueous Solution: Glyceraldehyde, Erythrose, Therose"; *Aust. J. Chem.*, vol. 33, pp. 1001-1011 (1980).

Choudry, G.A., et al; "A novel strategy for NQO1 (NAD(P)H:quinine oxidoreductase, EC 1.6.99.2) mediated therapy of bladder cancer based on the pharmacological properties of EO9"; *British Journal of Cancer*, vol. 85(8), pp. 1137-1146 (2001).

Gani, R., et al; "Method for selection of solvents for promotion of organic reactions"; *Computers & Chemical Engineering*; vol. 29, pp. 1661-1676 (2005).

Glushonok, G.K., et al; "A $^1$H and $^{13}$C NMR and UV Study of the State of Hydroxyacetone in Aqueous Solutions"; *Russian Journal of General Chemistry*, vol. 73, No. 7, pp. 1027-1031 (2003).

Huang, Mou-Tuan, et al; "Rat Liver Cytosolic Azoreductase"; *The Journal of Biological Chemistry*; vol. 254, No. 22, pp. 11223-11227 (1979).

March's Advanced Organic Chemistry, 5th Edition by Smith et al; John Wiley & Sons, Inc. (New York), pp. 327-362 (2001).

Soloniewicz, R., et al; "Spectrophotometric Determination of Reducing Sugars with Aromatic Nitro Compounds"; *Mikrochimica Acta I*; pp. 105-114 (1982).

Aghi, M., et al; "Prodrug activation enzymes in cancer gene"; *The Journal of Gene Medicine*; vol. 2, pp. 148-164.

Boland, M.P., et al; "The Differences in Kinetics of Rat and Human DT Diaphorase Result in a Differential Sensitivity of Derived Cell Lines to CB 1954 (5-(Aziridin-1-yl)-2,4-Dinitrobenzamide)"; *Biochemical Pharmacology*, vol. 41, No. 6/7, pp. 867-875 (1991).

Bridgewater, J.A., et al; "Expression of the Bacterial Nitroreductatse Enzyme in Mammalian Cells Renders Them Selectively Sensitive to Killing by the Prodrug CB1954"; *European Journal of Cancer*, vol. 31A, Nos. 13/14, pp. 2362-2370 (1995).

Buckner, F.S., et al; "Efficient Technique for Screening Drugs for Activity against *Trypanosoma cruzi* Using Parasites Expressing β-Galactosidase"; *Antimicrobial Agents and Chemotherapy*, vol. 40, No. 11, pp. 2592-2597 (1996).

Chung-Faye, G., et al; "Virus-directed, Enzyme Prodrug Therapy with Nitroimidazole Reductase: A Phase I and Pharmacokinetic Study of its Prodrug, CB1954[1]"; *Clinical Cancer Research*; vol. 7, pp. 2662-2668 2001).

Cobb, L.M., et al; "2,4-Dinitro-5-Ethyleneiminobenzamide (CB 1954): A Potent and Selective Inhibitor of the Growth of the Walker Carcinoma 256"; *Biochemical Pharmacology*, vol. 18, pp. 1519-1527 (1969).

Collins, J.M., et al; "Suicide Prodrugs Activated by Thymidylate Synthase: Rationale for Treatment and Noninvasive Imaging of Tumors with Deoxyuridine Analogues[1]"; *Clinical Cancer Research*, vol. 5, pp. 1976-1981 (1999).

Croft, S.L., et al; "Animal Models of Fisceral Leishmaniasis"; In *Handbook of Animal Models of Injection*, Zak, O. (ed), Academic Press, London, pp. 783-787 (1999).

Khan, A.H., et al; "Tumour-Growth Inhibitory Nitrophenylaziridines and Related Compounds: Structure-Activity Relationships"; *Chem-Biol. Interactions*; vol. 1, pp. 24-47 (1969).

Knox, R.J., et al; "A New Cytotoxic, DNA Interstrand Crosslinking Agent, 5-(Aziridin-1-yl)-4-Hydroxylamino-2-Nitrobenzamide, is Formed From 5-(Aziridin-1-yl)-2,4-Dinitrobenzamide (CB 1954) by a Nitroreductase enzyme in Walker Carcinoma Cells"; *Biochemical Pharmacology*, vol. 37, No. 24, pp. 4661-4669 (1988).

Knox, R.J., et al; "The Nitroreductase Enzyme in Walker Cells that Activates 5-(Azridin-1-yl)-2,4-Dinitrobenzamide (DB 1954) to 5-(Aziridin-1-yl)-4-Hydroxylamino-2-Nitrobenzamide is a Form of NAD(P)H Dehydrogenase (Quinone) (EC 1.6.99.2)*"; *Biochemical Pharmacology*, vol. 37, No. 24, pp. 4671-4677 (1988).

Knox, R.J., et al; "Bioactivation of CB 1954: Reaction of the Active 4-Hydroxylamino Derivative with Thioesters to Form the Ultimate DNA-DNA Interstrand Crosslinking Species"; *Biochemical Pharmacology*, vol. 42, No. 9, pp. 1691-1697 (1991).

Knox, R.J., et al; The bioactivation of DB 1954 and its use as a prodrug in antibody-directed enzyme prodrug therapy (ADEPT); *Cancer and Metatasis Reviews*, vol. 12; pp. 195-212 (1993).

Knox, R.J., et al; "CB 1954: From the Walker Tumor to NQO2 and VDEPT"; *Current Pharmaceutical Design*, vol. 9, pp. 2091-2104 (2003).

Loadman, P.M., et al; "Pharmacological Properties of a New Aziridinylbenzoquinone, RH1 (2,5-diaziridinyl-3-(hydroxymethyl)-6-methyl-1,4-benzoquinone), in Mice"; *Biochemical Pharmacology*, vol. 59, pp. 831-837 (2000).

Murray, H.W., et al; "Treatment of Experimental Visceral Leishmaniasis in a T-Cell-Deficient Host: Response to Amphotericin B and Pentamidine"; *Antimicrobial Agents and Chemotherpahy*; vol. 37, No. 7, pp. 1504-1505 (1993).

Pozas, R., et al; "Synthesis and in vitro antitrypanosomal activity of novel Nifurtimox analogues"; *Bioorganic & Medicinal Chemistry Letters*; vol. 15, pp. 1417-1421 (2005).

Smyth, T.P., et al; "S-Aminosulfeniminopenicillins: Multimode β-Lactamase Inhibitors and Template Structures for Penicillin-Based β-Lactamase Substrates as Prodrugs"; *J. Org. Chem.*, vol. 63, pp. 7600-7618 (1998).

Venitt, S., et al; "The toxicity and mutagenicity of the anti-tumour drug 5-aziridino-2,4-dinitrobenzamide (CB1954) is greatly reduced in a nitroreductase-deficient strain of *E. coli*"; *Mutagenesis*, vol. 2, No. 5, pp. 375-381 (1987).

Weedon, S.J., et al; "Sensitisation of Human Carcinoma Cells to the Prodrug CB1954 by Adenovirus Vector-Mediated Expression of *E. coli* Nitroreductase"; *Int. J. Cancer*, vol. 86, pp. 848-854 (2000).

Wei, Y., et al; "Activation of Antibacterial Prodrugs by Peptide Deformylase"; *Bioorganic & Medicinal Chemistry Letters*, vol. 10, pp. 1073-1076 (2000).

Woessner, R., et al; "Comparison of Three Approaches to Doxorubicin Therapy: Free Doxorubicin, Liposomal Doxorubicin, and β-Glucuronidase-Activated Prodrug (HMR 1826)"; *Anticancer Research*, vol. 20, pp. 2289-2296 (2000).

http://whqlibdoc.who.int/druginfo/19_2_2005_INN93.pdf; *WHO Drug Information*; vol. 19, No. 2 (2005).

METHOD OF COMBATING INFECTION

This application is the U.S. national phase of International Application No. PCT/GB2006/003252 filed 4 Sep. 2006 which designated the U.S. and claims priority to British Patent Application No. 0517957.7 filed 3 Sep. 2005, the entire contents of each of which are hereby incorporated by reference.

This invention relates to a method of combating infection and in particular to the treatment of parasitic protozoal infections The listing or discussion of a prior-published document in this specification should not necessarily be taken as an acknowledgement that the document is part of the state of the art or is common general knowledge.

BACKGROUND OF THE INVENTION

The incidence of drug-resistant parasitic protozoal diseases has grown significantly in recent years resulting in an increased number of deaths in both developing countries and the Western world. Strategies being developed to address the problem include the development of new drugs, the adoption of strict treatment regimens and a comprehensive public education programme.

A possible means for delivering highly active pharmacological agents to their site of action with minimal unwanted side effects in other cells and tissues is the use of prodrugs. Prodrugs have been known for many years and are used in several medical indications. They can be defined as chemical entities which are modified by metabolic or non-metabolic systems resulting in the formation or liberation of a species with the desired pharmacological activity. In many cases, prodrug forms are used to modify drug pharmacokinetics by the alternation of a physicochemical property of the drug (such as lipophilicity). In these cases, modification of the prodrug is generally non-specific, occurring by non-enzymatic degradative processes or by the metabolic action of ubiquitous enzymes. Prodrug forms may also be used, however, to target the active pharmacological agent to specific sites only, generally by exploiting the differential distribution of enzymes capable of catalysing the prodrug modification reaction.

In the field of cancer chemotherapy activation of prodrugs by target-specific enzymes has long been a goal and many potential prodrugs have been synthesised and tested in the hope that a tumour-specific enzyme would be capable of converting them specifically into a potent anti-tumour agent.

Many researchers are still active in this area utilising prodrugs designed to be activated by a variety of enzymes including β-glucuronidase (Woessner et al (2000) *Anticancer Research* 20, 2289-2296), DT diaphorase (Loadman et al (2000) *Biochemical Pharmacology* 59, 831-837) and thymidylate synthase (Collins et al (1999) *Clinical Cancer Research* 5, 1976-1981).

As an alternative to this prodrug monotherapy strategy some researchers have attempted to deliver the desired enzyme to the tumour, prior to administering a prodrug. Such an approach, often termed antibody-directed enzyme prodrug therapy (ADEPT), has been disclosed in WO88/07378. In this example the enzyme is linked to a monoclonal antibody which is capable of binding to a tumour-associated antigen. In this way the enzyme is delivered to the tumour site where it can act on an appropriate prodrug. A similar strategy has been disclosed, for example, in WO 96/03151, in which the gene encoding an enzyme is delivered to the tumour and, once present, expresses the desired enzyme. This strategy is often termed gene-directed enzyme prodrug therapy (GDEPT).

It is an important tenet of many of these targeting strategies that the enzyme delivered to the tumour site should not be endogenous to the host (Aghi et al (2000) *J Gene Med* 2, 148-164). The presence of endogenous enzymes would lead to non-specific activation of the prodrugs and toxicity to normal tissues. Accordingly, the majority of these enzyme-prodrug therapy studies have been carried out using bacterial enzymes such as carboxypeptidase G2, β-lactamase and nitroreductase.

Whilst much of the work to date in the field of site-specific prodrug activation has concentrated on anticancer therapy, there have been recent efforts to adapt this technology for use in antibacterial applications. For example, WO 99/32113 describes the use of prodrugs consisting of a cytotoxic moiety and a β-lactam moiety. In Gram-negative bacteria containing β-lactamase enzymes within the periplasmic space, the prodrug is cleaved to release the cytotoxic moiety which then goes on to disrupt vital cell functions. These prodrugs are limited in their breadth of applicability, however, in that not all bacteria express β-lactamases and in that Gram-positive bacteria tend to excrete β-lactamases such that much of the beneficial toxin-locating effect of the prodrug will be lost.

In Smyth et al ((1998) *J. Org. Chem.* 63, 7600-7618), the S-aminosulfenimino-penicillins are introduced. These compounds are both β-lactamase inhibitors and potential prodrug templates for the delivery of a variety of agents into β-lactamase-positive bacteria. As with the β-lactam-derivatives discussed above, however, these compounds are likely to be of limited utility in Gram positive bacteria and, due to their slow permeation through outer membrane porin structures, may need to be present at undesirably high extracellular concentrations in order to achieve significant effects in Gram-negative bacteria.

A departure from the potential shortcomings of β-lactamase-dependent prodrugs has been presented by Wei and Pei ((2000) *Bioorg. Med. Chem. Lett.* 10, 1073-1076). These workers conceptually demonstrated the use of 5'-dipeptidyl derivatives of cytotoxic antibacterial agents as prodrugs activatable by bacterial peptide deformylase. Preliminary results using these prodrugs suggested rather weak antibacterial activity, however, and it was hypothesised that this may have been due to poor uptake of the compounds into cells.

Human parasitic diseases are endemic in many parts of the world. For example, leishmaniasis (a parasitic disease caused by an obligate intracellular protozoan transmitted by the bite of some species of sand flies) is found in approximately 90 tropical and subtropical countries around the world and in southern Europe. More than 90% of the world's cases of, cutaneous leishmaniasis are in Afghanistan, Algeria, Brazil, Iran, Iraq, Peru, Saudi Arabia, and Syria. However, approximately 75% of the cases that are evaluated in the United States were acquired in Latin America, where leishmaniasis occurs from northern Mexico (occasionally in rural southern Texas) to northern Argentina. More than 90% of the world's cases of visceral leishmaniasis occur in Bangladesh, Brazil, India, Nepal, and Sudan. Similarly, the geographical distribution of Chagas' Disease (caused by a flagellate protozoan parasite, *Trypanosoma cruzi*, transmitted to humans by triatomine insects) extends from Mexico to the south of Argentina. The disease affects 16-18 million people and some 100 million, i.e. about 25% of the population of Latin America, is at risk of acquiring Chagas' disease. Even people staying for a short time in parasite-endemic areas can become infected and parasitic diseases are becoming a problem in the developed world as a result from the increase in global travel.

Resistance to the presently used drugs has been reported. Problems of resistance require the use of more toxic drugs and as the drugs are becoming less and less effective new drug discovery is needed.

SUMMARY OF THE INVENTION

The inventors have now found that, surprisingly, nitroreductase enzymes also appear to be expressed in certain parasitic protozoal organisms and the inventors suggest that tretazicar may be highly effective against parasitic infestation in animals (such as humans) because the animal (eg human) host is insensitive to this agent while the parasite will be toxically affected. The inventors have now shown that tretazicar is extremely effective against certain protozoal parasites and so it is an object of the invention to provide tretazicar as a highly effective anti-parasitic agent.

A first aspect of the invention provides a method of combating a parasitic protozoal infection of a host organism, the method comprising administering tretazicar to the host organism.

The host organism preferably is an animal, more preferably a mammal and most preferably a human. Non-human mammals for treatment by the method of the invention include horses, cows, pigs, goats, sheep, dogs, cats and the like.

By "combating" the given infection we include the meaning that the infection is substantially eradicated or that the infection is substantially inhibited. It will be appreciated that it may not be necessary for all parasites in the host organism to be killed in order to effectively treat the host organism.

A second aspect of the invention provides a use of tretazicar in the manufacture of a medicament for combating a parasitic protozoal infection of an animal.

The compound tretazicar is (5-(aziridin-1-yl)-2,4-dinitrobenzamide (CB1954)), whose structure is shown below. Tretazicar has been used previously as an anticancer agent.

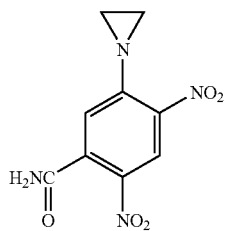

Tretazicar has the registry number C.A.S. No 21919-05-1 and its synthesis has been described in Khan & Ross (1969/70) "Tumour growth inhibitory nitrophenylaziridines and related compounds: structure-activity relationships" *Chem-Biol Interactions* 1, 27-47 and in Cobb et al (1969) *Biochem. Pharmacol.* 18, 1519-1527.

This compound is capable of eradicating a specific rat tumour ('Walker tumour'), though has little or no effect upon a variety of other tumours (Cobb et al (1969) *Biochem. Pharmacol.* 18, 1519-1527) and shows no therapeutic benefit in clinical oncology studies (Knox et al (1993) *Cancer and Metastasis Rev.* 12, 195-212). It has been shown that a nitroreductase enzyme present in the Walker tumour is capable of activating CB1954 by reducing its 4-nitro group to form the compound 5-aziridino-4-hydroxylamino-2-nitrobenzamine, a potent electrophilic DNA cross-linking agent in the presence of intracellular thioesters (Knox et al (1988) *Biochem. Pharmacol.* 37, 4661-4669; Knox et al (1991) *Biochem. Pharmacol.* 42, 1691-1697). The corresponding enzyme in human cells has relatively slow kinetics of reduction, thus rendering human cells insensitive to the effects of CB1954 (Boland et al (1991) *Biochem. Pharmacol.* 41, 867-875).

In mechanistic studies in bacteria, it has been shown that CB1954 has attenuated toxicity in nitroreductase-negative strains (Venitt and Crofton-Sleigh (1987) *Mutagenesis* 2, 375-381).

Tretazicar is activated to form an antiparasitic agent by protozoal parasite-associated enzymes. The term "protozoal parasite-associated enzyme" means an enzyme or isoform thereof which is either specific to the protozoal parasite constituting the infection, or is expressed in a functional form to such a low extent by the host organism as to render any activation of tretazicar by the latter insufficient to cause unacceptable host toxicity, but which enzyme is expressed by the protozoal parasite.

Typically, the parasite-associated enzyme is at least 10-fold or 20-fold or 50-fold or 100-fold or 500-fold or 1000-fold more active at activating the compound than an enzyme present in the host organism.

It will be appreciated that tretazicar is substantially unchanged by enzymes endogenous to the host organism and is activated substantially by one or more enzymes in the protozoal parasite.

By "activated to form an antiparasitic agent" we include the meaning that tretazicar is converted to a form which is cytotoxic, particularly to the protozoal parasite.

Similarly, it will be appreciated that the methods and medicaments of the invention are particularly suited to combat protozoal parasite infection wherein the protozoal parasite is one which contains an enzyme system which is able to activate tretazicar into a substantially cytotoxic form. A method for determining whether a protozoal parasite is responsive to tretazicar is described in the Example. Such protozoal parasites may be killed by tretazicar. Suitably, protozoal parasitic infections which may be treated with tretazicar are ones for which tretazicar has an $IC_{50}$ of less than 10 micromolar preferably less than 5 micromolar and more preferably less than 1 micromolar.

Other methods of determining if a protozoal parasite contains an enzyme capable of activating tretazicar to a substantially cytotoxic form will be known to those skilled in the art. These include, but are not limited to, the use of suitable computer programs, for example the GAP program of the University of Wisconsin Genetic Computing Group, to compare the gene sequence of the protozoa with that of known nitroreductase-containing species or the use of classical techniques whereby the relevant enzyme is detected, isolated and purified prior to testing with tretazicar.

Tretazicar is believed to be capable of covalently cross-linking protozoal parasite nucleic acid once it has been activated by an enzyme system present in the parasite to the cytotoxic form. Since tretazicar only becomes so capable on activation by a parasite-associated enzyme, the presence of tretazicar in host cells is believed not to pose a danger since they do not possess compatible enzyme activity. Binding of tretazicar to host cell components via the aziridine (or mustard) group, will present only a minor risk of cell disruption since any mono-functionally bound compound is believed to be excisable by host repair enzymatic processes (Knox et al (2003) *Current Pharmaceutical Design* 9, 2091-2104).

The parasite-associated enzyme responsible for activating the compound has, we believe, nitroreductase activity, for example under both oxic and hypoxic conditions.

In one embodiment, tretazicar may be used to selectively inhibit those parasites which have developed resistance to one or more currently used antibiotics.

In one embodiment of the invention, the animal is also administered one or more other compounds known to be of use in combating a parasitic infection.

Tretazicar and one or more other compounds as stated may be administered together or sequentially.

Compounds known to be of use in combating a parasitic infection include Misonidazole, nitroheterocyclics such as Nifurtimox and RSU 1069, Benznidazole antimonials such as stibogluconate, and acetylcholine derivatives such as Miltefosine.

Thus, further aspects of the invention provide use of a combination of tretazicar and one or more other compounds known to be of use in combating a parasitic infection of an animal in the manufacture of a medicament for combating a parasitic infection of an animal; and use of tretazicar in the manufacture of a medicament for combating a parasitic infection of an animal, wherein the animal is administered one or more other compounds known to be of use in combating a parasitic infection of an animal; and use of one or more other compounds known to be of use in combating a parasitic infection of an animal in the manufacture of a medicament for combating a parasitic infection of an animal, wherein the animal is administered tretazicar.

The methods and medicaments of the invention find particular utility in combating infections with one or more of *Trypanosoma cruzi*, *T. brucei*, *Leishmania* spp. particularly *L. infaritum*, *Cryptosporidium* spp. and *Giardia* spp.

A further aspect of the invention provides the combination of tretazicar with one or more other compounds known to be of use in combating a protozoal parasitic infection of a host organism.

The combination may be packaged and presented for use in medicine.

In a further embodiment, the combination may be further combined with a pharmaceutically acceptable carrier in order to form a pharmaceutical composition. A pharmaceutical composition may include, for example, tretazicar and sterile, pyrogen-free water. Typically, the pharmaceutical composition is in a liquid form in polyethyleneglycol/N-methylpyrrolidone (PEG/NMP) diluted with saline (Chung-Faye et al (2001) *Clinical Cancer Research* 7, 2662-2668).

A preferred embodiment is a pharmaceutical composition for oral administration. Conveniently, the pharmaceutical composition is a gelatine capsule containing the tretazicar. Typically, the pharmaceutical composition is a capsule or tablet which allows enteric release, for example by virtue of a coating which dissolves in the intestine. Methods of making such capsules and tablets are well known in the art.

The one or more compounds as defined may be administered to the host organism in any suitable form and in any amount effective to combat the infection. Suitably, the veterinary (in the case of non-human animals) or medical (in the case of humans) practitioner can select the appropriate route of administration and the appropriate dose or dosing regime. An amount of tretazicar is administered, either as single or multiple doses, in an amount effective to combat the parasitic infection.

For administration to an animal (including human), appropriate routes of administration include but are not limited to intravenous, transdermal and by inhalation. Typically, for administration to a human by infusion, the tretazicar would be administered at a dose of up to 30 mg/m$^2$. Oral administration is also suitable, such as using a gelatine capsule as discussed above.

The tretazicar may be given by a variety of routes depending on the nature and location of the infective agent. Accordingly, a variety of compositions of different pharmaceutical form are provided, as would be clear to one skilled in the art.

BRIEF DESCRIPTION OF THE DRAWINGS

The invention will now be described in more detail by reference to the following Figures and non-limiting example.

EXAMPLE 1

Antiparasitic Activity of Tretazicar

In Vitro Activity

Tretazicar was screened against a number of parasitic organisms using an integrated in vitro screening system and compared against the treatment of choice against that organism (Table 1).

As shown in Table 1, tretazicar is extremely active against *Leishmania infantum* and *Trypanosoma cruzi* and is much more active than the established agents. Cytotoxicity assays against a range of human cell lines always give an IC$_{50}$ value>50 μM and the therapeutic ratios against these two organisms is thus dramatic (>16,000 for *T. cruzi* and >625 for *L. infantum*). Although not as potent as suramin, tretazicar was active against *T. brucei* with a therapeutic ratio>10. No activity was seen against the tested strains of *T. colubriformis* or *Plasmodium falciparum* presumably because they do not express an enzyme system which is able to activate tretazicar into a cytotoxic form.

Given the proven clinical acceptability of tretazicar, this agent represents a novel prodrug approach for the treatment of parasitic infestation, in particular leishmaniasis and Chagas' disease.

TABLE 1

In vitro data for tretazicar against certain parasites

| | *T. cruzi* (tulahuen CL2) IC$_{50}$ μM |
|---|---|
| Nifurtimox | 0.45 |
| Tretazicar | 0.003 |
| | *L. infantum*, IC$_{50}$ μM |
| Stibogluconate | 6.0 |
| Tretazicar | 0.08 |
| | *T. b. brucei*, IC$_{50}$ μM |
| Suramin | 0.045 |
| Tretazicar | 5.0 |
| | *T. colubriformis*, IC$_{50}$ μM |
| Albendazole | 0.002 |
| Tretazicar | >32 |
| | *P. falciparum* (Ghana), IC$_{50}$ μM |
| Chloroquine | 0.018 |
| Tretazicar | >32 |

In Vivo Activity

In vivo activity of tretazicar against *L. donovani* was tested in both BALB/c and SCID mice. The infection and treatment of the animals was performed as described by Croft and Yardley and references there in (Croft & Yardley (1999) Animal models of visceral leishmaniasis. In Handbook of Animal Models of Infection, Zak, O. (ed) pp 783-787, Academic Press, London). At the end of treatment the mice were weighted to give an estimation of drug toxicity. The liver was removed from freshly sacrificed animals and weighed. Smears were then prepared from the livers on microscope slides and fixed with methanol and stained with Giemsa stain. The number of parasites per 500 liver cells was determined microscopically for each experimental animal. This figure is multiplied by total liver weight (mg) and this figure (the Leishman-Donovan unit (LDU)) is used as the basis for calculating the difference in parasite load between treated and untreated animals (Croft & Yardley, 1999 supra).

Figure 1:
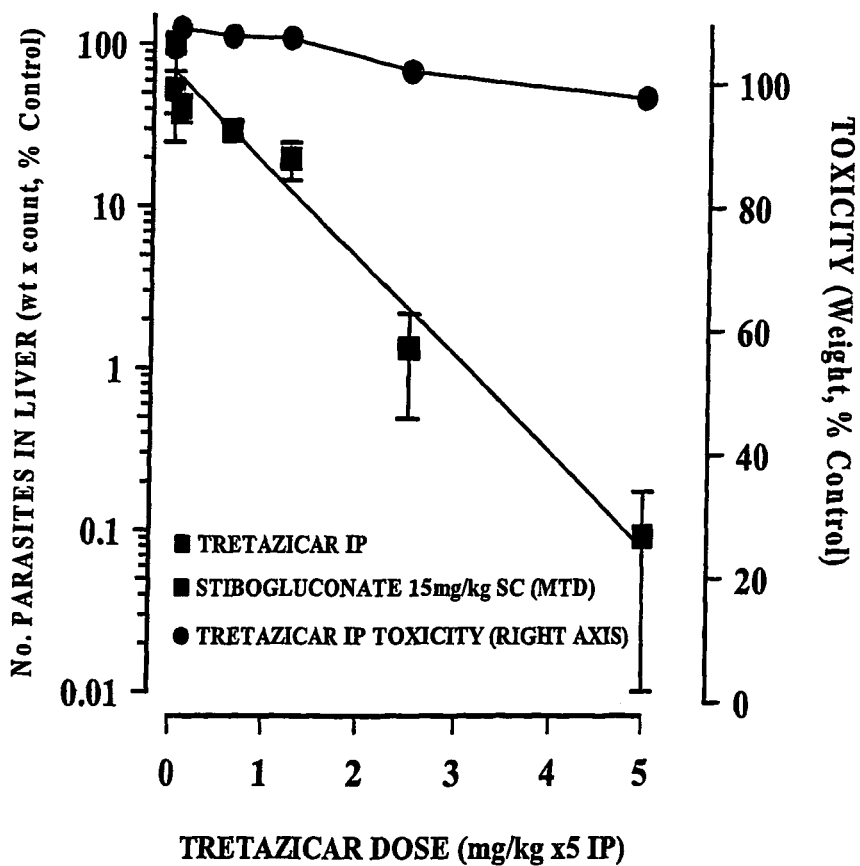
FIG. 1 shows the activity of tretazicar against *L. donovani* HU3 in BALB/c mice (daily IP administration).
Figure 2:
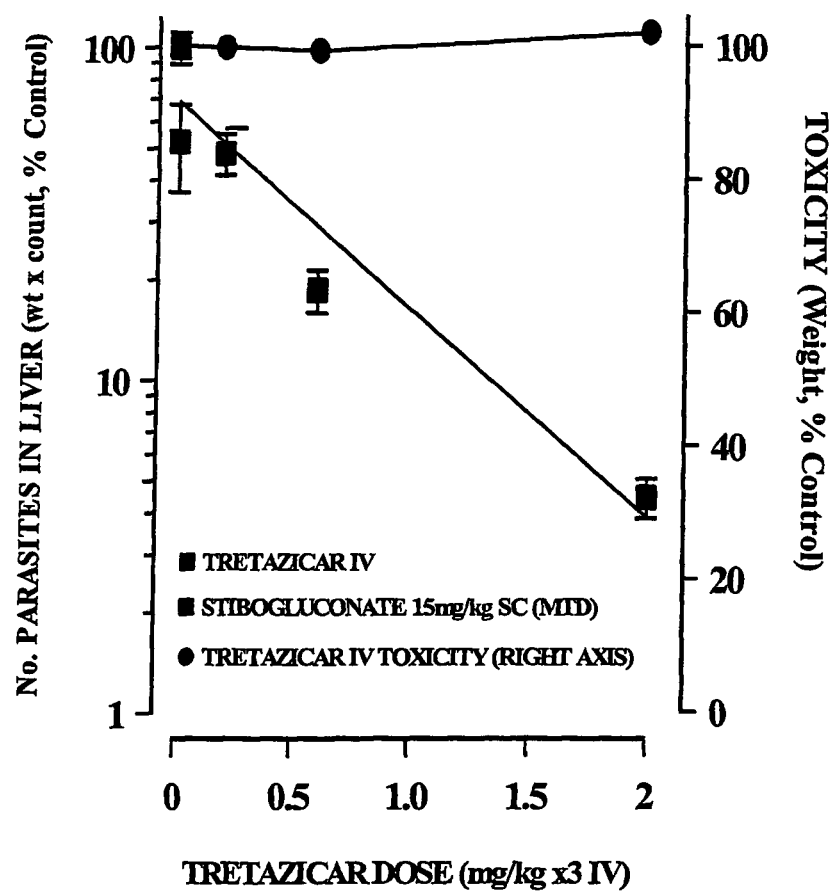
FIG. 2 shows the activity of tretazicar against *L. donovani* HU3 in BALB/c mice (daily IV administration).
Figure 3:
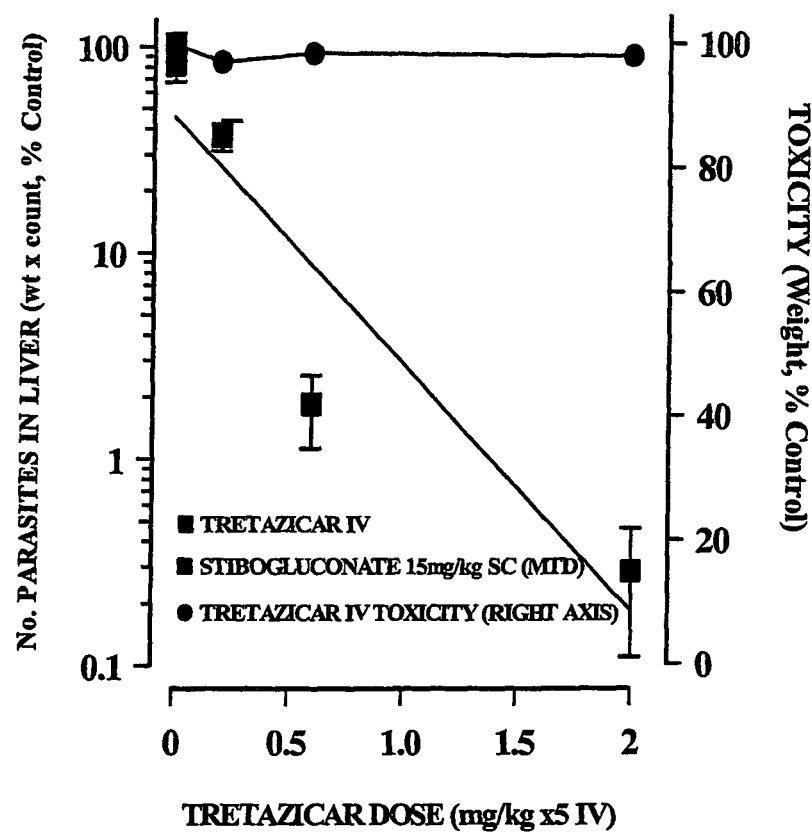
FIG. 3 shows the activity of tretazicar against *L. donovani* HU3 in SCID mice (daily IV administration).

As shown in FIGS. 1 to 3, there is a dramatic log/linear dose response of inhibition of parasite numbers with tretazicar concentration. No drug related toxicity, as measured by body weight loss, was observed in these experiments and significant toxicity was not observed until a dose of 10 mg/kg×5 was employed. $ED_{50}$ values obtained are shown in Table 2. The equivalent activity of tretazicar in both BALB/c and immunodeficient SCID mice shows that the therapy is not immune dependent. This would be predicted from the proposed mechanism of action. Stibogluconate at its MTD (15 mg/kg×5 SC) was used as the control compound for these experiments. This dose only achieved a 52±15.2% inhibition in parasite counts in BALB/c mice and little effect in the SCID mouse model. The in vivo efficacy of stibogluconate is known to be T cell dependent (Murray et al (1993) *Antimicrob. Agents Chemother.* 37, 1504-1505). The activity of tretazicar is notably higher than standard anti-leishmanial drugs in mouse models (compare data in Table 1 with that in Croft & Yardley, 1999 supra).

Tretazicar is also effective against *T. cruzi* in vivo. As shown in Table 3, infected but untreated BALB/c mice only survived for an average of 13.8 days. At a dose of 0.3 mg/kg (IP×5, daily) all the mice survived for the 50 days before the experiment was terminated. However at this dose parasites could still be detected in the blood at 13 days. A dose of 3.0 mg/kg (IP×5, daily) cleared all the parasites from the blood. A dose of 45 mg/kg (p.o.×5 daily) of benznidazole was required to produce an equivalent effect

TABLE 2

Activity of Tretazicar against *L. donovani* HU3

| Mouse Strain | Treatment | $ED_{50}$ mg/Kg | $ED_{90}$ mg/Kg |
|---|---|---|---|
| BALB/c | IP × 5 Daily | 0.23 | 1.41 |
| BALB/c | IV × 3 Daily | 0.19 | 1.15 |
| SCID | IV × 5 Daily | 0.18 | 0.35 |

TABLE 3

Activity of Tretazicar against *T cruzi*.

# of type of field, X = day of death

| Group # | compound ID | dosing regimen | Mouse # | 6 14/03 | 7 15/03 | 8 16/03 | 9 17/03 | 10 18/03 | 11 19/03 | 12 20/03 | 13 21/03 | 14 22/03 | 15 23/03 | 16 24/03 | 26 03/04 | 51 27/04 |
|---|---|---|---|---|---|---|---|---|---|---|---|---|---|---|---|---|
| 1 | untreated control | | 1 | 0/20 | | | | | | | 1/10 | | X | | 13.8 | |
| | | | 2 | 0/20 | | | | | | | 35/10 | X | | | | |
| | | | 3 | 3/20 | | | | | | | X | | | | | |
| | | | 4 | 2/20 | | | | | | | X | | | | | |
| | | | 0 | 1/20 | | | | | | X | | | | | | |
| 2 | benznidazole | 45 mg/kg p.o. x5 | 1 | 0/20 | | | | | | | 0/10 | | | | | All |
| | | | 2 | 3/20 | | | | | | | 0/10 | | | | | mice |
| | | | 3 | 3/20 | | | | | | | 0/10 | | | | | killed |
| | | | 4 | 4/20 | | | | | | | 0/10 | | | | | |
| | | | 0 | 1/20 | | | | | | | 0/10 | | | | | |
| 10 | Vehicle alone | i.p. x5 | 1 | 1/20 | | | | | | | X | | 13 | | | |
| | | | 2 | 0/20 | | | | | X | | | | | | | |
| | | | 3 | 2/20 | | | | | | | X | | | | | |
| | | | 4 | 2/20 | | | | | X | | | | | | | |
| | | | 0 | 0/20 | | | | | | | 2/5 | X | | | | |
| 11 | Tretazicar | 0.3 mg/kg i.p. x5 | 1 | 2/20 | | | | | | | 16/5 | | | | X | All |
| | | | 2 | 0/20 | | | | | | | 2/5 | | | | | mice |
| | | | 3 | 0/20 | | | | | | | 2/5 | | | | | killed |
| | | | 4 | 0/20 | | | | | | | 7/5 | | | | | |
| | | | 0 | 0/20 | | | | | | | 6/5 | | | | | |
| 12 | Tretazicar | 1 mg/kg i.p. x5 | 1 | 0/20 | | | | | | | 0/10 | | | | | All |
| | | | 2 | 0/20 | | | | | | | 0/10 | | | | | mice |
| | | | 3 | 0/20 | | | | | | | 3/10 | | | | | killed |
| | | | 4 | 1/20 | | | | | | | X | | | | | |
| | | | 0 | 1/20 | | | | | X | | | | | | | |
| 13 | Tretazicar | 3 mg/kg i.p. x5 | 1 | 5/20 | | | | | | | 0/10 | | | | | All |
| | | | 2 | 12/20 | | | | | | | 0/10 | | | | | mice |
| | | | 3 | 4/20 | | | | | | | 0/10 | | | | | killed |
| | | | 4 | 1/20 | | | | | | | 0/10 | | | | | |
| | | | 0 | 1/20 | | | | | | | 0/10 | | | | | |
| 14 | Tretazicar | 10 mg/kg i.p. x5 | 1 | 0/20 | | | | | | | 0/10 | | | | | All |
| | | | 2 | 1/20 | | | | | | | 0/10 | | | | | mice |
| | | | 3 | 0/20 | | | | | | | 0/10 | | | | | killed |
| | | | 4 | 0/20 | | | | | | | 0/10 | | | | | |
| | | | 0 | 2/20 | | | | | | | 0/10 | | | | | |

Given the proven clinical acceptability of tretazicar, this agent represents a novel prodrug approach for the treatment of parasitic infestation, in particular leishmaniasis and Chagas' disease.

In Vitro Screening Methods

Chagas' Disease: In Vitro Screening Model *T. cruzi* (MHOM/CL/00/Tulahuen); *T. cruzi* (MHOM/BR/00/Y)

Parasite and Cell Cultures

The *Trypanosoma cruzi* (MHOM/CL/00/Tulahuen) transfected with β-galactosidase (Lac Z) gene, was used (Buckner et al (1996) *Antimicrobial Agents and Chemotherapy* 40(11), 2592-2597. The strain was maintained on an L-6 (rat skeletal myoblast cell line obtained from European Collection of Animal Cell Cultures (ECACC, Salisbury, UK)) cell-layer in RPMI 1640 w/o phenol red medium supplemented with 10% heat inactivated fetal calf serum. All cultures and assays were conducted at 37° C. under an atmosphere of 5% $CO_2$ in air.

Drug Sensitivity Assays

Stock tretazicar solutions were prepared in 100% DMSO (dimethylsulfoxide) at 20 mg/ml. The stocks were kept at room temperature in the dark prior to use. For the assays, the compound was further diluted to the appropriate concentration using complete medium.

Assays were performed in sterile 96-well microliter plates, each well containing 100 μl medium with $2 \times 10^3$ L-6 cells. After 24 hours 50 μl of a trypanosome suspension containing $5 \times 10^3$ trypomastigote bloodstream forms from culture was added to the wells. 48 hours later the medium was removed from the wells and replaced by 100 μl fresh medium with or without a serial drug dilution. After 72 hours of incubation the plates were inspected under an inverted microscope to assure growth of the controls and sterility, and to determine the minimum inhibitory concentration (MIC): this is the lowest drug concentration at which no trypanosomes with normal morphology as compared to the control wells can be seen. Nifurtimox was used as the reference drug.

The substrate CPRG/Nonidet (50 μl) was added to all wells. A colour reaction became visible within 2-6 hours and was read photometrically at 540 nm. The results, expressed as % reduction in parasite burdens compared to control wells, were transferred into a graphic programme (EXCEL), sigmoidal inhibition curves determined and $IC_{50}$ values calculated.

Primary Screen

The compounds were tested in triplicate at 4 concentrations (30-10-3-1 μg/ml). Nifurtimox was included as the reference drug.

The compound is classified as inactive when the $IC_{50}$ is higher than 15 μg/ml. When the $IC_{50}$ lies between 15 and 5 μg/ml, the compound is regarded as being moderately active. When the $IC_{50}$ is lower than 5 μg/ml, the compound is classified as highly active and is further evaluated in a secondary screening.

Secondary Screen

The same protocol was used and the $IC_{50}$s determined using an extended dose range adjusted as appropriate.

Leishmaniasis: In Vitro Screening

Parasite and Cell Cultures

One strain of *Leishmania* spp. (*Leishmania donovani* MHOM/ET/67/L82, also known as LV9,HU3) was used. The strain is maintained in the Syrian Hamster (*Mesocricetus auratus*). Amastigotes were collected from the spleen of an infected hamster and spleen parasite burden was assessed using the Stauber technique.

Primary peritoneal mouse (CD1) macrophages were collected 1 or 2 days after a macrophage production stimulation with an i.p. injection of 2 ml 2% soluble starch. All cultures and assays were conducted at 37° C. under an atmosphere of 5% $CO_2$.

Drug Sensitivity Assays 20 mg/ml tretazicar stock solution was prepared in 100% DMSO and was kept at room temperature in the dark. The stock was pre-diluted to 60 μg/ml in RPMI 1640+10% heat inactivated fetal calf serum. Assays were performed in sterile 16-well tissue culture slides, each well containing 50 μl of the compound dilutions together with 100 μl of macrophage/parasite inoculum ($4 \times 10^5$ macrophages/ml and $4 \times 10^6$ parasites/ml). The inoculum was prepared in RPMI-1640 medium, supplemented with 10% heat inactivated fetal calf serum. Parasite growth was compared to control wells (100% parasite growth). After 5 days of incubation, parasite growth was microscopically assessed after staining the cells with a 10% Giemsa solution. The level of infection/well was evaluated by counting the number of infected macrophages per 100 macrophages. The results expressed as % reduction in parasite burden compared to control wells, were transferred into a graphic programme (EXCEL), sigmoidal inhibitions curves determined and $IC_{50}$ values calculated.

Primary Screen

The compounds were tested in quadruplicate at 4 concentrations (30-10-3-1 μg/ml). Pentostam® (sodium stibogluconate) was included as the reference drug.

The compound is classified as inactive when the $IC_{50}$ is higher than 15 μg/ml. When the $IC_{50}$ lies between 15 and 5 μg/ml, the compound is regarded as being moderately active. When the $IC_{50}$ is lower than 5 μg/ml, the compound is classified as highly active and is further evaluated in a secondary screening.

Secondary Screen

The same protocol was used and the $IC_{50}$ determined using an extended dose range adjusted as appropriate. Pentostam® was included as the reference drug.

The invention claimed is:

1. A method of combating a parasitic protozoal infection of a host organism, wherein the parasite causing the infection is associated with an enzyme system capable of activating tretazicar into a cytotoxic form, the method comprising administering tretazicar to the host organism.

2. A method according to claim 1 wherein the host organism is an animal.

3. A method according to claim 2 wherein the animal is a mammal.

4. A method according to claim 3 wherein the mammal is a human.

5. A method according to claim 1 wherein the enzyme is a nitroreductase.

6. A method according to claim 1 wherein the host organism is one which does not contain endogenously an enzyme system which activates tretazicar to such an extent as to cause unacceptable toxicity to the host organism or animal.

7. A method claim 1 wherein the parasite causing the infection is antibiotic resistant.

8. A method according to claim 1 wherein the parasitic infection of the organism is caused by any one or more of the following parasites: *Trypanosoma cruzi, T. brucei, Leishmania* spp., *Cryptosporidium* and *Giardia* spp.

9. A method according to claim 8 wherein the parasitic infection of the organism is caused by any one or more of the following parasites: *Trypanosoma cruzi, T. brucei* and *Leishmania infantum*.

10. A method according to claim 1 wherein the host organism is also administered one or more other compounds known to be of use in combating a parasitic infection.

11. A combination of tretazicar and one or more other compounds known to be of use in combating a protozoal parasitic infection of a host organism.

12. A combination according to claim 11 wherein the host organism is an animal.

13. A pharmaceutical composition comprising the combination as defined in claim 12 and a pharmaceutically acceptable carrier.

\* \* \* \* \*